(12) United States Patent
Rahman et al.

(10) Patent No.: US 11,918,346 B2
(45) Date of Patent: Mar. 5, 2024

(54) METHODS AND SYSTEMS FOR PULMONARY CONDITION ASSESSMENT

(71) Applicant: Samsung Electronics Company, Ltd., Suwon-si (KR)

(72) Inventors: Md Mahbubur Rahman, San Jose, CA (US); Ebrahim Nematihosseinabadi, Mountain View, CA (US); Viswam Nathan, Mountain View, CA (US); Korosh Vatanparvar, Mountain View, CA (US); Md Juber Rahman, Mountain View, CA (US); Soujanya Chatterjee, Mountain View, CA (US); Nazir Saleheen, Mountain View, CA (US); Jilong Kuang, Mountain View, CA (US); Jun Gao, Mountain View, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 429 days.

(21) Appl. No.: 16/792,057

(22) Filed: Feb. 14, 2020

(65) Prior Publication Data

US 2021/0045656 A1 Feb. 18, 2021

Related U.S. Application Data

(60) Provisional application No. 62/885,754, filed on Aug. 12, 2019, provisional application No. 62/885,743, filed on Aug. 12, 2019.

(51) Int. Cl.
*A61B 5/087* (2006.01)
*A61B 5/11* (2006.01)

(52) U.S. Cl.
CPC .......... *A61B 5/0871* (2013.01); *A61B 5/1118* (2013.01)

(58) Field of Classification Search
CPC ....... A61B 5/08; A61B 5/0803; A61B 5/0816; A61B 5/082; A61B 5/0823; A61B 5/0833;
(Continued)

(56) References Cited

U.S. PATENT DOCUMENTS 7,094,206 B2 8/2006 Hoffman
9,307,944 B2 4/2016 Colman
(Continued)

FOREIGN PATENT DOCUMENTS

KR 20190037848 A 4/2019
WO WO-2010116276 A1 * 10/2010 ........... A61B 5/0002
(Continued)

OTHER PUBLICATIONS

International Search Report and Written Opinion for PCT application No. PCT/KR2020/007395, dated Sep. 16, 2020.

*Primary Examiner* — Matthew Kremer
*Assistant Examiner* — Om Patel

(57) ABSTRACT

In particular embodiments, a method includes accessing, by a computing device, sensor data from a sensor of a client device corresponding to a user. The method further includes determining one or more segments of sensor data and selecting at least one segment of sensor data. The method further concludes determining, based at least on the selected segments of sensor data, one or more features corresponding to the user's pulmonary condition. The method further includes determining, based at least on the determined features, an assessment of the user's pulmonary condition.

19 Claims, 5 Drawing Sheets

(58) Field of Classification Search
CPC ....... A61B 5/0836; A61B 5/085; A61B 5/087;
A61B 5/0871; A61B 5/0897; A61B
5/1118; A61B 5/113; A61B 5/1135
See application file for complete search history.

(56) References Cited

U.S. PATENT DOCUMENTS

| | | | |
|---|---|---|---|
| 9,993,166 B1 * | 6/2018 | Johnson | A61B 5/0022 |
| 10,028,675 B2 | 7/2018 | Patel | |
| 11,129,536 B2 | 9/2021 | Freeman | |
| 2006/0111754 A1 | 5/2006 | Rezai | |
| 2012/0150054 A1 | 6/2012 | Abe | |
| 2015/0065893 A1 * | 3/2015 | Ye | A61B 5/0205 |
| | | | 600/595 |
| 2017/0332993 A1 | 11/2017 | Asai | |

FOREIGN PATENT DOCUMENTS

| | | | |
|---|---|---|---|
| WO | WO 2018107008 A1 | 6/2018 | |
| WO | WO-2019089830 A1 * | 5/2019 | A61B 5/0022 |

* cited by examiner

METHODS AND SYSTEMS FOR PULMONARY CONDITION ASSESSMENT

PRIORITY

This Application claims priority under 35 U.S.C. § 119 to provisional patent application No. 62/885,754 and to provisional patent application No. 62/885,743, which are incorporated by reference herein.

TECHNICAL FIELD

This disclosure generally relates to electronically detecting pulmonary conditions.

BACKGROUND

According to the American Lung Association, more than 35 million people are living with chronic pulmonary diseases, including chronic obstructive pulmonary disease (COPD) and asthma. COPD refers to a class of lung ailments that cause difficulty in breathing which progressively leads to serious complications and can prove fatal. Asthma causes breathlessness during asthma attacks. Both COPD and asthma cannot be cured, and if left unchecked can severely affect quality of life and ultimately prove fatal; COPD is the third leading cause of death in the United States. However, these illnesses can be managed with proper medication, especially if detected in the early stages. Early detection of lung worsening for chronic pulmonary patients reduces hospital readmissions and improves patient outcomes and quality of life.

Pulmonary conditions affect walking ability and can manifest as sound events such as coughing, wheezing, throat clearing, and can also affect speech. This is because the condition of an individual's pulmonary health affects voice production and speech patterns. If the airways are obstructed, or if there is irregular air flow to the vocal cords, vocal production may deviate from the expected norm. As actions required to produce speech essentially provoke a relatively higher respiratory drive compared to breathing in silence, pulmonary conditions can lead to alterations of speech patterns.

Pulmonary conditions may be assessed using a specialized device called a spirometer. A tube is inserted into a patient's mouth and an expert guides the patient to blow their exhale to the maximum. This Pulmonary Function Test (PFT), a common test for assessing the severity of a patient's lung condition, is normally done under supervision of a clinical expert. A peak flow meter is another test which measures one isolated parameter, such as how quickly the patient can exhale.

Another commonly used test for cardio-pulmonary patients is the 6-Minute Walk Test (6MWT). Distance in a 6MWT over a 100 m track is used as a minimum clinically important difference (MCID). However, this test is done when the patient visits a clinical facility to meet their pulmonologist or primary care physician. Both PFT and 6MWT are cumbersome tests that are not accessible outside of a clinical facility.

DESCRIPTION OF EXAMPLE EMBODIMENTS

Figure 1:
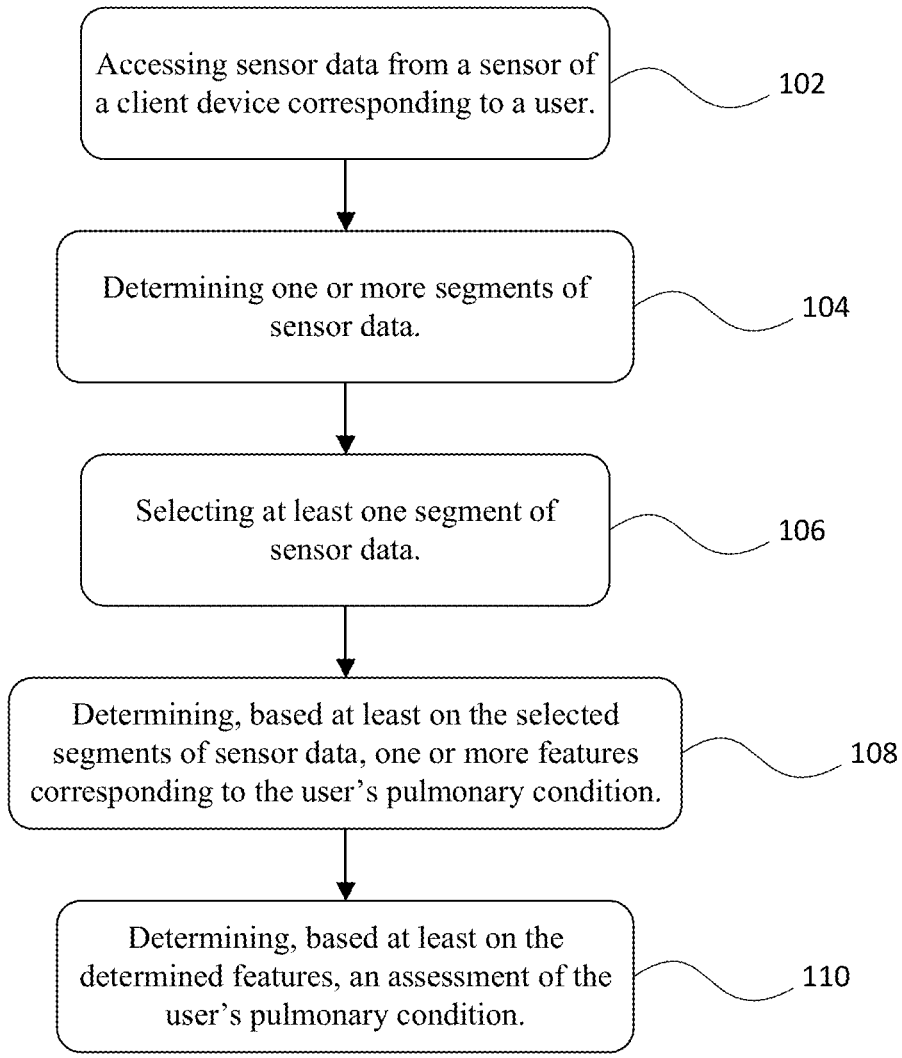
FIG. 1 illustrates an example method for detecting pulmonary condition.

The methods and systems of this disclosure utilize a user's natural speech and reduce the need for cumbersome devices and the presence of an expert by enabling passive assessment by client devices, such as mobile devices. Particular embodiments may assist users in assessing their lung condition with an easy-to-follow, low-effort protocol at home. As an example, particular embodiments may extract vocalized vowel sound segments during the user's natural speech, eliminating the need for the user to produce a sustained vowel sound.

Particular embodiments include passive assessment of pulmonary condition without a spirometer and without an intentional 6MWT. Such assessments may be continuous over a period of time, may be user or clinician activated, may occur periodically, or any suitable combination thereof. Particular embodiments may enable passive assessment based on differential features related to detected activities performed in everyday life. Particular embodiments may determine a combination of features related to pulmonary function from low-effort assessment activities. Particular embodiments may passively assess pulmonary condition and, based on such assessments, may trigger active assessments when it is determined that passive assessment indicates a pulmonary condition or that passive assessments are not adequately determining pulmonary conditions.

Pulmonary assessment techniques can extract physiological parameters from sensor data to measure a user's pulmonary condition. In particular embodiments, the pulmonary assessment may be a passive assessment that monitors the user's activity in the background. For example, the assessment may access sensor data of a client device corresponding to a user and, based on the data, extract features related to the user's pulmonary condition. In particular embodiments, the pulmonary assessment may include an active assessment. For example, the assessment may prompt the user to provide user data by performing an activity.

Particular embodiments of the methods and systems disclosed herein continuously assess pulmonary condition by segmenting and analyzing sensor data, such as data captured by a mobile device. Passive assessment techniques can include leveraging activities by the user as the user engages in daily activities. For example, embodiments may be able to detect walking activity, speech activity, or both. These activities may be captured by a mobile device, such as a smartphone, smartwatch, or other wearable device. As explained herein, these activities correspond to the user's pulmonary condition in that they can be used to assess the user's pulmonary condition. When the mobile device captures or accesses user activity, the same device can extract physiological parameters that are relevant to the user's pulmonary condition. These parameters can be used to assess the user's pulmonary condition without demanding that the user engage in activities explicitly for detecting pulmonary condition, such as the 6MWT.

In particular embodiments, passive assessment may be complemented by active assessment. Active assessment can be an on-the-spot assessment. There may be a frequency threshold for the aggregate amount, consistency, or number of passive assessments within a predetermined time period such that active assessment is performed if the threshold(s) for passive assessments are not met. The time period for the threshold could be the past few days, weeks, or months and could be configured based on recommendations defined by, e.g., medical experts, such as a patient's medical care provider. As an example, the system may determine whether there are fewer than a threshold number of passive assessment events within a time period. If in this example, there are fewer than the threshold number of passive assessment events for the given time period, the system may trigger an on-the-spot active assessment request for the user to provide data related to the user's pulmonary condition. As an example, if in particular embodiments the device cannot identify any data segments representative walk or speech activity for passive assessment in a predetermined period of time, then the system may trigger an active assessment.

Particular embodiments of this invention access sensor data from a user's mobile device and process that sensor data by filtering for noise or quality. The sensor data may be segmented into data segments corresponding to user activity or events relevant to pulmonary assessment. Features relevant to pulmonary assessment are extracted from the segments of sensor data. Pulmonary condition is assessed based on the features and segments. The features and segments may also be used to analyze a trend or detect deterioration of lung condition.

FIG. 1 illustrates an example method for detecting pulmonary condition. At step 102, the method includes accessing sensor data from a sensor of a client device corresponding to a user. At step 104, the method includes determining one or more segments of sensor data. At step 106, the method includes selecting at least one segment of sensor data. At step 108, the method includes determining one or more features. As illustrated in step 108, the one or more features may be determined based at least on the selected segments of sensor data. At step 110, the method includes determining a pulmonary assessment of the user's pulmonary condition. As illustrated in step 110, the user's pulmonary condition may be based at least on the determined features.

Sensor data may be accessed from one or more sensors of a client device. Particular embodiments may access data from sensors of more than one device, such as sensors on a user's smartphone and sensors on a user's smartwatch. The sensor data may be captured from a client device, such as a smartwatch or a smartphone, and the sensors may be embedded in the client device, although this disclosure contemplates that sensor data may be stored by devices other than those containing the sensors, such as a server device. In particular embodiments, sensors operate continuously and passively in order to obtain sensor data that may be accessed in, e.g., step 102 of FIG. 1. Particular embodiments can use sensor data from sensors that duty cycle, for example, to save battery consumption. Moreover, this disclosure contemplates that sensors from which data is accessed may include both low-power sensors that can operate continuously and more power-consuming sensors that can operate in a duty cycle. As an example, a low-power motion sensor can trigger a more power-intensive PPG sensor and/or audio sensor (e.g., a microphone) when the motion sensor passively detects pulmonary assessment related activities, such as walking or movements associated with speech.

The sensor data accessed in, e.g., step 102 of FIG. 1 may include motion sensor data, heart sensor data, acoustic sensor data, or data from any other suitable sensor. Motion sensor data can come from motion sensors on the client device. Motion sensors can include 3-axis accelerometers, 3-axis gyroscopes, and 3-axis magnetometers and their derivative signals. For example, motion sensor data may include linear acceleration data, rotational motion derived from a gyroscope, directional motion derived from a magnetometer, or any suitable combination thereof. In particular embodiments, to obtain linear acceleration data the gravity component may be removed from the raw data collected by an accelerometer.

Sensor data can be obtained by sampling at the rate of 20 Hz, although this disclosure contemplates higher or lower sampling frequencies. Sampling frequency can be adaptive, for example to save battery consumption. For example, a user's motion can be sensed using a motion sensor sampling at a baseline 20 Hz sample rate, while the sampling rate can be 50 Hz or more when an activity relevant to pulmonary assessment is being detected (e.g., walking). A motion sensor may take data such as an inertial measurement unit (IMU) to sense motion from the user's whole body, such as motion associated with or resulting from walking, or motion of a part of the body, such as motion associated with or resulting from breathing. A motion sensor may also detect speaking activity, for example based on hand gestures that may occur during a conversation.

Heart sensor data can include one or more of: heart rate (HR), heart rate variability (HRV), poincare plot, oxygen saturation (SpO2), or breathing rate (BR). Particular embodiments may use a photoplethysmogram (PPG) sensor. Sensors may include optical heart rhythm sensors embedded on mobile devices such as a smartphone or a smartwatch. Optical sensing on a smartwatch, for example, can passively sense relevant physiological features during, before, and after pulmonary assessment activity segments. For heart rate variability, particular embodiments may use a sampling frequency of 100 Hz. This sampling frequency may be adapted to motion-sensing-based activity detection, for example to preserve the device's battery. As an example, particular embodiments may sample at 20 Hz or not sample at all as a default setting, and sample at 100 Hz when activities relevant to pulmonary assessment are detected. As an example, a heart-rate sensor may not collect data until the client device detects that the user is walking or speaking. At that point, the heart rate sensor may begin to collect data, or collect data at a different frequency than it was before. While the above example references a heart sensor, this disclosure contemplates that any suitable sensor may begin or change sampling in response to detection of pulmonary-related activities.

Acoustic sensor data can come from, e.g., a microphone sensor on a client device. In particular embodiments, sampling frequency can vary from 10 kHz to 44 kHz based on the type of activities being detected. A microphone may sample data in mono or stereo to sense the user speech and/or the environmental sound, for example to better understand the user's context, such as other sources of noise in the user's environment. Acoustic sensing may be more power consuming than other types of sensing, and therefore acoustic sensing can be triggered by, e.g., a low-power motion sensor on the device.

Particular embodiments may interpret one or more segments of data as. The one or more segments of data may be selected for extraction of pulmonary features or pulmonary assessment. The one or more segments may be selected based on selection criteria, which may include one or more of: the length of the segment, the amount of noise in the segment, the condition of the segment data, whether the segment contains sufficient data for performing pulmonary assessment, and the presence or absence of speech characteristics. A segment may be discarded if it does not contain sufficient data collected from the user, e.g. if the contribution of pulmonary-assessment data in the segment is relatively low as compared to other collected segments. Segment selection may be based on motion sensor data, acoustic sensor data, or any data from any other sensor or combination of sensors.

Particular embodiments may include an admission control unit that removes noise from sensor data, such as PPG and acoustic data, and passes the de-noised signal for further processing. In particular embodiments, a motion artifact may be the main source of noise in a signal from a PPG sensor. As an example, motion may be detected using 3-axis accelerometer data. Motion may be detected by computing the magnitude of motion for a particular time window, and by computing the standard deviation (std) of each magnitude. An example time window may be one second. The PPG noise handler may determine noise by detecting whether the std feature is greater than a predetermined threshold. In particular embodiments, an admission control unit can mark the PPG signal as noisy for the window in which the std feature is greater than the threshold. The threshold may be learned from statistical population data or may be calibrated from data related to the user, or both.

In particular embodiments, sound may be sampled from one or more microphones embedded in device, such as a smartphone, smartwatch, or smartspeaker. Particular embodiments may analyze the sound samples to determine whether or not there is speech activity. If there is no speech activity present in the sound segment, that data segment may be discarded, i.e., it is not used for further processing by the methods and systems disclosed herein. If there is speech activity, then embodiments may determine whether the sensor data associated with speech environment has noise. In general, speech of the user in a noisy environment may be more indicative of pulmonary condition than speech in a quiet environment, because the user must generally speak louder to be heard in a noisy environment, and speaking loudly requires exertion of greater effort. In addition, conditions affecting lung condition may be better captured when the user is exerting greater effort to speak. In particular embodiments, samples of microphone activity may be selected for pulmonary assessment based on the presence or absence of factors indicating that the user is speaking with greater effort. For example, embodiments may identify whether the user is one or more of: speaking loudly, speaking in a noisy environment, speaking with a raised voice, speaking to a group of people, or speaking while the television is on.

Particular embodiments may detect the amount of contribution the user makes to a conversation. A conversation between two or more people may be detected in one or more sound samples, and sound samples of the conversation may be considered candidates for pulmonary assessment of the user. Particular embodiments may differentiate between when the user is speaking and when other people are speaking. Detection of which person in a conversation is speaking may be based on the intensity of a given segment of speech (i.e. particular embodiments may differentiate speakers based on the relative intensity of their speech). For example, the user may be closest to the wearable device, and thus the user's speech may have the highest intensity. Particular embodiments may determine the amount of speech per minute that the user contributed to the conversation, and the user's rate of speech per minute within a sound segment may be used to determine whether the sound segment is to be selected for pulmonary assessment.

In particular embodiments, speech activity may be detected by applying voice activity detection (VAD) techniques to sound samples. An algorithm based on Long-Term Spectral Divergence (LTSD) may be implemented. A given sound sample may be split into individual frames, and the frames may be processed in a non-overlapping manner. Individual frames may be of length 20 ms each. An algorithm may require a "noise spectrum" estimate (i.e. a spectrum of recorded sound containing no speech activity). Particular embodiments may determine the 5% of total individual frames of the given sound sample that contain the lowest detected energy and use those frames to estimate the "noise spectrum." Particular embodiments may be configured to handle misclassifications of individual frames after an initial application of a VAD technique. Misclassification occurs when an individual frame containing speech activity is mistakenly classified as not containing speech activity, or when an individual frame not containing speech activity is mistakenly classified as containing speech activity. There may be one or more individual frames of one class between a plurality of consecutive frames of the other class. Particular embodiments may assume a minimum pause time of 250 ms, or a minimum speech time of 100 ms. Based on an assumed minimum pause time or speech time, particular embodiments may automatically iterate over all frames in the given segment and re-classify individual frames to meet the assumptions.

The boundaries of detected pause segments may be checked for statistically unexpected rises in energy, which could be indicative that the detected pause segments contain the edges of a segment of speech activity. Particular embodiments may perform a statistical z-test on energies of individual frames of a given detected pause segment and reclassify as voice segments frames with energy of a Z-score higher than a given threshold. The threshold of particular embodiments may be a Z-score of 2. Particular embodiments may compare the energy of detected pause segments with the energy of a set of all pause segments detected for the user in the aggregate. A pause segment with energy that is markedly higher than a threshold Z-score when compared to other pause segments in the set may be re-classified as a voice segment. The threshold Z-score for analysis of the set of pause segments in the aggregate may be empirically chosen based on examination of the user's data.

In particular embodiments, one or more segments of the sensor data may be selected for pulmonary assessment. Pulmonary assessment may occur passively and continuously, and segments may be selected from sensor data collected from activities performed during the user's daily life. Particular embodiments may use motion sensor data, acoustic data, or both motion sensor and acoustic data to determine whether and if the user is engaged in an activity that is relevant to pulmonary assessment. Relevant activities that could be detected include: speaking, walking, and a combination of speaking and walking. Activities can be detected using classification models based on features extracted from data from the motion sensors and the acoustic sensors over a certain window (e.g., 1 second). Motion sensor features that may be classified include mean, standard deviation, kurtosis, skewness of zero crossing rate, accelerometer magnitude, gyroscope magnitude, energy, entropy and the like. Acoustic features that may be classified include zero crossing rate, energy, root means square, mel-frequency cepstral coefficients, chroma vector, pitch, tone, entropy, spectrogram features and the like.

Activities may be selected or segmented, and data representing particular segments of an activity may be selected for pulmonary assessment. Activities may be segmented based on one or more criteria. For example, if there is a pause in an activity such as walking or speaking, that pause may create two different activity segments. However, if the pause is below a certain threshold, then in particular embodiments those two activity segments may be treated as part of the same activity. If a pause is above the threshold, then those two different segments may be treated as two different segments. Pause thresholds may be different for walking activity and speech activity. For speech activity, particular embodiments may determine whether a pause in speech activity is due to the user pausing for breath or due to cognitive pause (e.g. the user having finished vocalizing a thought), for example based on the length of pause and/or associated sounds (e.g., a user inhaling or exhaling).

Particular embodiments may determine whether or not one or more activity segments can be utilized for pulmonary assessment. As an example, if an activity segment has sufficient walking data or speech data, then that segment may be selected for assessment. Otherwise, a segment or segments without sufficient walking or speech data may be discarded. In particular embodiments, activities may be determined, segmented, and analyzed in real time as they occur. In particular embodiments, activities may be determined, segmented, and analyzed with some delay after they occur. In particular embodiments, data representing an activity segment without sufficient walking or speech data may be discarded, and the embodiments may wait for another activity to occur. For example, if the detected activity is walking activity, particular embodiments may determine the length of the walking segment and the number of steps per minute taken by the user. Either or both of length of the walking segment and the user's number of steps per minute may be used to determine whether the walking segment is selected and used for pulmonary assessment.

Particular embodiments may process selected data segments and assess the user's pulmonary condition. Assessment of pulmonary condition may include extracting features related to pulmonary assessment from the selected data segments, analyzing the extracted features, estimating pulmonary obstruction, and estimating severity of the obstruction. In particular embodiments, the user's pulmonary condition may be assessed in real time, while other embodiments may determine the user's pulmonary condition sometime after an activity has occurred.

Extracted features may include primal and differential features. Extracted features may include physiological parameters (HR, HRV, BR, and SpO2, for example) and features relating to the activity performed by the user (cadence or distance walked, for example). Primal features may include respiration rate, inhale-exhale ratio, walking distance, walking speed, speech production rate, inhalation sound pattern, breathing pattern, heart rate, heart rate variability, oxygen saturation (SpO2), dyspnea, fatigue, cough frequency, cough violence, and/or recovery pattern. Physiological parameters may include respiration rate, heart rate variability, their differences before and after walking or speech, gait speed, and speech production rate. Extracted features may include pause features (e.g., durations of pause for breath and the frequency of these pauses) and prosodic features (e.g., shimmer and jitter).

Human speech consists of sharp inhalation prior to vocalization, followed by continuous exhalation during vocal production. When respiratory functions are compromised, this can lead to longer inhalation times, a feature referred to herein as "pause time." Pause time for the user may be the average pause time from the set of all pause segments detected for the user in the aggregate, expressed in milliseconds. Pause time may be the average pause time from a set of pause segments detected for the user within a given period of speech activity (e.g., the average pause time from a set of pause segments from the duration of one detected conversation). Alternatively, difficulty in breathing can also manifest as more frequent pauses in order to satisfy a more frequent need for inhalation, a feature referred to herein as "pause frequency." Pause frequency may be the average number of pauses the user takes per minute of speech activity.

Pulmonary conditions can also affect tonal qualities of human speech, e.g., by affecting the consistency of localized vocal amplitude for voiced vowel sounds. Changes in prosodic features of speech, such as shimmer and jitter, therefore may be symptomatic of pulmonary illnesses. Shimmer refers to the consistency of localized vocal amplitude for voiced vowel sounds and is a measure of cycle-to-cycle variations in sound waveform amplitude. Jitter refers to the consistency of localized periodicity for voiced vowel sounds and is a measure of cycle-to-cycle variations in sound frequency. Each of a speaker's voiced vowel sounds has a different fundamental period. The following sections illustrates example techniques for measuring shimmer and jitter.

For a given voiced vowel sound segment, absolute shimmer is the average difference in amplitudes between peaks of the dominant component (representative of the fundamental frequency), expressed in decibels. The example equation below illustrates one technique for calculating absolute shimmer, where N is the number of periods of the fundamental waveform in the segment, and $A_i$ is the amplitude of the i-th peak of the fundamental waveform in the segment.

$$\frac{1}{N-1}\sum_{i=1}^{N-1} |20 \log_{10} A_{i+1}/A_i|$$

For a given voiced vowel sound segment, relative shimmer is the average difference in amplitudes between the peaks of consecutive periods, relative to the overall amplitude of the peaks, expressed as a percentage. The example equation below illustrates one technique for calculating relative shimmer, where N is the number of periods of the fundamental waveform in the segment, and $A_i$ is the amplitude of the i-th peak of the fundamental waveform in the segment.

$$\left( \frac{\frac{1}{N-1}\sum_{i=1}^{N-1} |A_i - A_{i+1}|}{\frac{1}{N}\sum_{i=1}^{N} A_i} \right) \times 100$$

For a given voiced vowel sound segment, absolute jitter is the average difference between consecutive periods of the fundamental waveform (i.e. variations in the fundamental frequency between each period, expressed in microseconds. The example equation below illustrates one technique for calculating absolute jitter, where N is the number of periods of the fundamental waveform in the segment, and $T_i$ is the duration of the i-th period of the fundamental waveform in the segment.

$$\frac{1}{N-1}\sum_{i=1}^{N-1}|T_i - T_{i+1}|$$

For a given voiced vowel sound segment, relative jitter is the average difference between consecutive periods of the fundamental waveform relative to the overall average period, expressed as a percentage (i.e. relative jitter is absolute jitter relative to the average period for the given vowel segment). The example equation below illustrates one technique for calculating relative jitter, where N is the number of periods of the fundamental waveform in the segment, and $T_i$ is the duration of the i-th period of the fundamental waveform in the segment.

$$\left(\frac{\frac{1}{N-1}\sum_{i=1}^{N-1}|T_i - T_{i+1}|}{\frac{1}{N}\sum_{i=1}^{N} T_i}\right) \times 100$$

Particular embodiments may determine the most viable vowel sounds for extraction of prosodic features by selecting speech activity segments with energy in, e.g., the 95th percentile of the set of speech activity segments for the user, in the aggregate. Particular embodiments may select segments of duration meeting or exceeding a threshold duration. For example, the threshold duration may be 80 ms. A duration requirement ensures that there are a sufficient number of periods in the segment for analysis of jitter and shimmer. Particular embodiments may determine a segment's dominant frequency. The dominant frequency may be between 70 Hz and 300 Hz, as measured by power spectral density. This range of frequencies covers a spectrum of human voice production across genders. In particular embodiments, the dominant frequency may be used to guide a peak detection algorithm that estimates the amplitude and time difference between each of the periods of the fundamental frequency to calculate shimmer and jitter.

Particular embodiments may cluster a set of shimmer and jitter values for a given vowel sound segment using hierarchical clustering to identify outliers. A maximum within-cluster distance may be set to 1 dB, 15%, 200 microseconds, and 500 microseconds for the peak-to-peak values of absolute shimmer, relative shimmer, absolute jitter, and estimated period, respectively. The estimated period between each peak may be used to estimate the average period, which in turn may be used to calculate relative jitter. The maximum within-cluster distances may be chosen empirically based on manual observation of the range of occurrence of outliers in a given set of data. Particular embodiments may perform a check on the set of average shimmer or average jitter values for each segment to ensure that they do not exceed reasonable physiological limits. Reasonable physiological limits may be 0-30%, 0-3 dB, 0-16%, and 10-1000 microseconds for relative shimmer, absolute shimmer, relative jitter, and absolute jitter, respectively. Particular embodiments may perform a statistical Z-score test on each set of average shimmer or average jitter values, and may discard values above a Z-score threshold, where the Z-score threshold may be 3.

Any or all of the features described herein may be extracted from one or more of the selected data segments. The features extracted, particularly the physiological features, may vary based on the user's pulmonary condition or severity. The features extracted may vary based on the activity the user performed in one or more of the selected data segments. As an example, one set of features may be extracted from a selected data segment during which the user performed an activity, and a different set of features may be extracted from a selected data segment during which the user performed a different activity. For example, as explained above, walking cadence or distance may be extracted from data corresponding to a walking activity, while shimmer and jitter analysis may be extracted from data corresponding to a speech activity. In particular embodiments, the features may be extracted from a specified window of time of sensor data. As an example, features may be extracted in a specified time window of one minute, or in a specified time window of 30 seconds. In particular embodiments, features may be extracted by further segmenting the selected data segments into smaller time windows. As an example, a selected data segment of ten minutes of user walking activity may be further segmented into 10 one-minute time windows. In this example, features may be extracted for one or more of the ten one-minute time windows. Particular embodiments may analyze the one or more of the ten one-minute time windows for statistical aggregation of the features and estimate the robustness of the pulmonary assessment.

Differential features may be extracted by analyzing changes in primal features or physiological parameters over one or more periods of time. Differential features may include differences between primal features from a plurality of different time periods. Particular embodiments may calculate differential features by comparing primal features from before and after a data segment of an activity related to pulmonary condition such as walking, speaking, or walking and speaking. Differential features may also include differences in primal features between the start of an activity and a subsequent part or end of the same activity. Differential features may also include differences in primal features between a previous pulmonary assessment and the current pulmonary assessment.

In particular embodiments, differential features may be extracted before a data segment and after a data segment. Differential features may allow more accurate estimation of the severity of a user's pulmonary changes. Differential features may allow particular embodiments to capture the user's physiological changes that are caused by the user's performing a particular activity. Differential features allow particular embodiments to capture personalized variation in pulmonary features, making pulmonary assessment more accurate. Particular embodiments may use any suitable algorithm to extract differential features. One or more algorithms may also be used to determine an optimal combination of features to determine pulmonary condition.

Particular embodiments may make an assessment of the user's pulmonary condition based at least on the determined features. This assessment may include measuring or estimating pulmonary obstruction and severity of the obstruction. Particular embodiments may use machine learning models, including regression or classification models, to assess the user's pulmonary condition.

Models used may estimate whether the user has any lung obstructions by estimating FEV1/FVC ratio. Once an obstruction is determined, the model used may further analyze the selected data segments to determine the severity of the obstruction by estimating the user's FEV1% predicted number. FEV1% may be estimated based on the user's FEV1 volume, age, gender, and height and may be based on the user's baseline condition as determined by, e.g., an active assessment.

Particular embodiments may visually display the estimated pulmonary obstruction by color: red (severe), yellow (moderate), green (mild) visualization. Particular embodiments may compute a confidence value of the assessment. The confidence value may be due to user preferred variation. The pulmonary assessment and confidence value may be used in combination to determine the needs of the user or may be used to assist clinicians in determining the needs of the user. Particular embodiments may determine whether the user needs to have a clinical spirometer test conducted or whether the user needs to visit their primary care physician. Particular embodiments may trigger active assessment to confirm the pulmonary condition's severity as detected by passive monitoring. In these embodiments, active assessment may reduce false alarms from passive monitoring.

Particular embodiments may aggregate selected segments over a predefined period of time. For example, one embodiment may aggregate segments every six hours to generate a trend over the course of a day. Another embodiment may aggregate segments each day to generate a trend of pulmonary health, such as deterioration, over the course of a week or month. In particular embodiments, there may be a threshold number of passive assessments needed to calculate a trend. Based on a determination that the number of passive assessments meets or exceeds the threshold number, a trend may be created. The trend may be based on the current or most recent passive assessment and/or one or more previous assessments. Generated trends may be used by the user or their caregiver to diagnose the user and/or adapt the user's treatment to their changing condition. Generated trends may track the severity of the user's pulmonary condition over time and may be used to determine the rate of deterioration. Particular embodiments may notify the user or their caregiver when FEV1% is determined to be below a predetermined threshold of deterioration.

Figure 2:
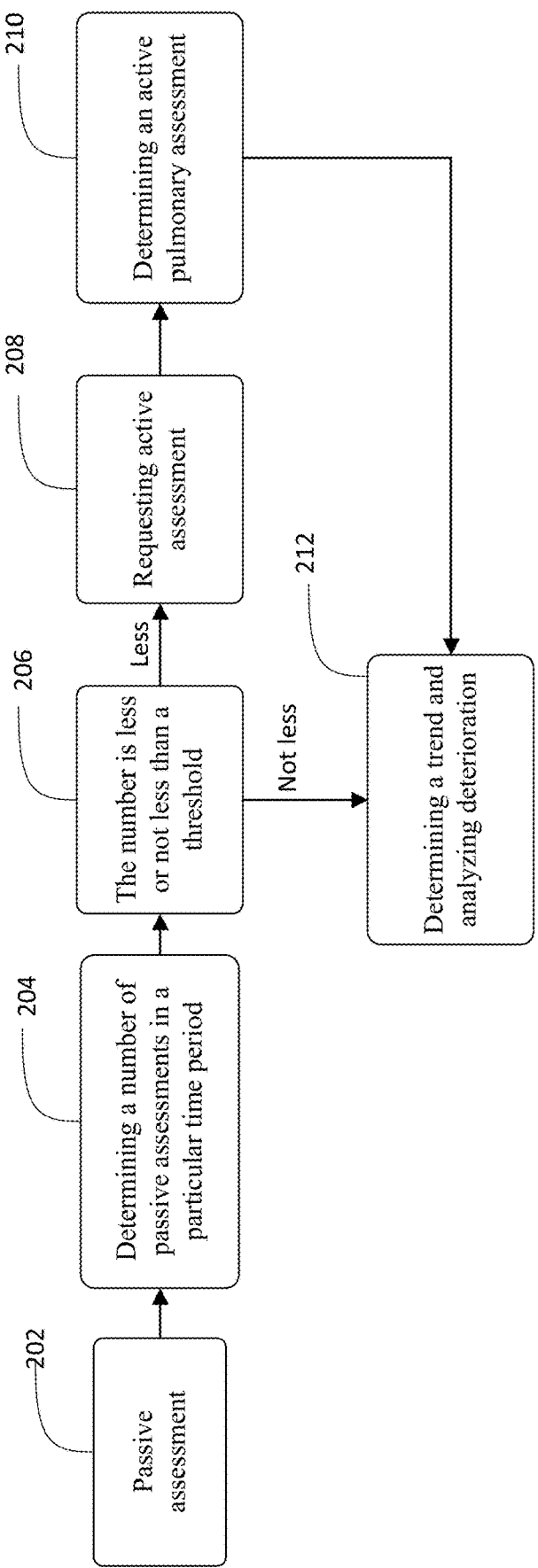
FIG. 2 illustrates an example diagram for assessment of user pulmonary condition.

Particular embodiments may determine a triggering condition that triggers an active assessment. An active assessment may be automatically triggered when triggering conditions are satisfied. FIG. 2 illustrates an example diagram for assessment of a user's pulmonary condition. As illustrated in FIG. 2, a passive assessment may be obtained in step 202. FIG. 2 illustrates that particular embodiments may determine the number of passive assessments in a particular time period in step 204. In step 206, there may be a determination that the number of passive assessments in the particular time period is less or not less than a threshold. As illustrated in FIG. 2, if the number is not less than the threshold, a trend of deterioration may be determined in step 212. As illustrated in FIG. 2, if the number is less than the threshold, an active assessment may be requested in step 208. As illustrated in FIG. 2, a condition for an active assessment may be based on a lack of activity sensor data for a passive assessment. A condition for an active assessment may also be based on a trend of deterioration of pulmonary condition over time.

Active assessment may include automatically prompting the user to perform active assessment tasks, capturing data from user-performed tasks, extracting features from the data, and determining lung condition. Particular embodiments may select and extract optimal features based on the tasks performed by the user and combine the optimal features to assess pulmonary condition. In particular embodiments, extracting optimal features may be based on k-fold cross-validation on ground truth (empirically observed) data collected from hospital-grade devices. Particular embodiments may also determine the quality of the inferences based on the tasks selected or features extracted. As illustrated in FIG. 2, step 210 comprises determining an active pulmonary assessment. As illustrated in FIG. 2, step 212 comprises determining a trend and analyzing deterioration.

Figure 3:
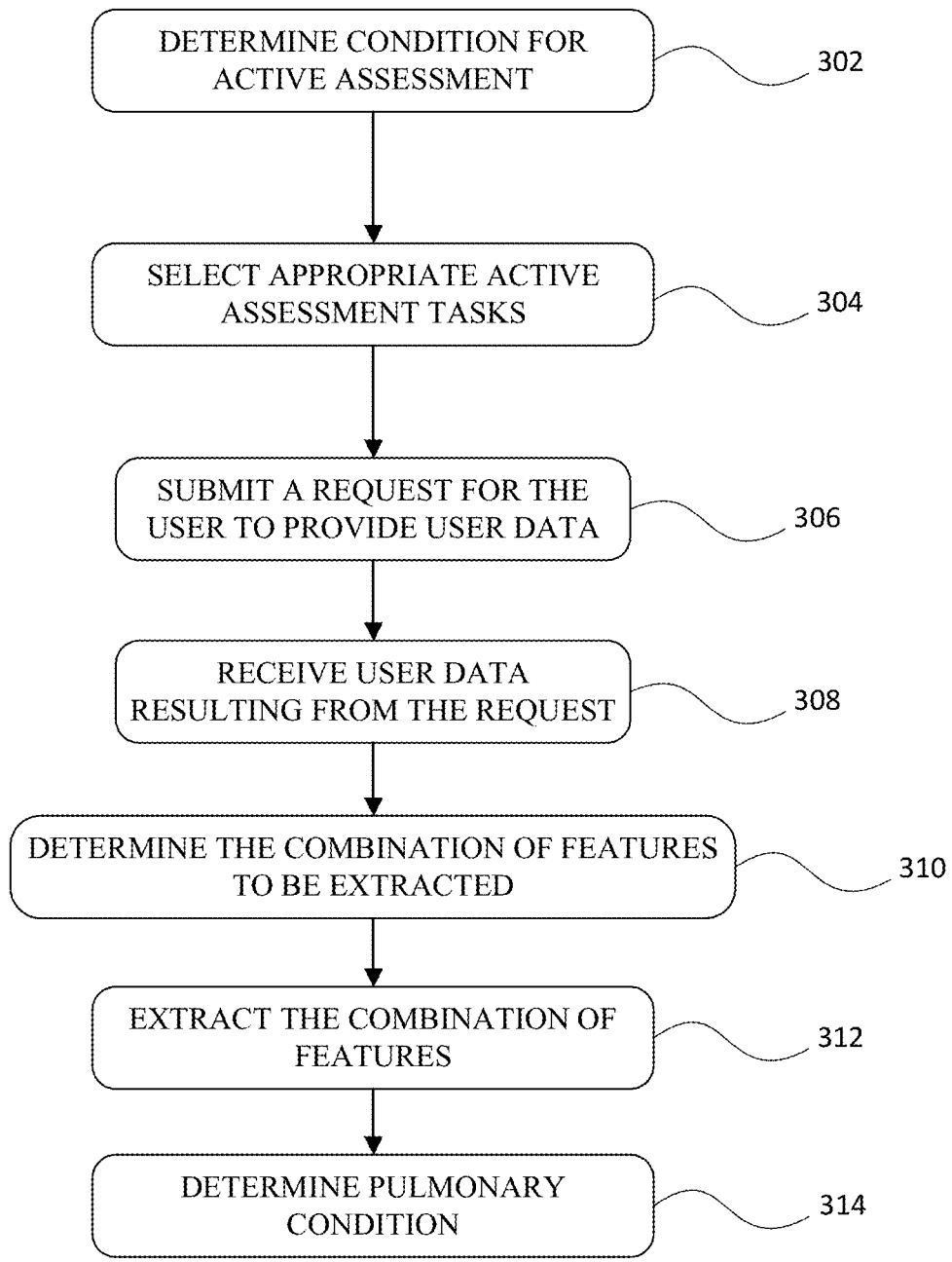
FIG. 3 illustrates example steps executed by an example active assessment protocol.

FIG. 3 illustrates example steps executed by an example active assessment protocol. Step 302 may determine a condition for active assessment. Step 304 may select one or more assessment tasks. Such tasks may include one or more of tidal breathing, A-vowel sound, speech, reading, blowing exhale into a sensor of a device, or a 6MWT. As an example, particular embodiments may select appropriate assessment tasks for the user to perform based on the user's determined pulmonary condition. Particular embodiments may select an assessment task based on the user's pulmonary condition or pulmonary symptoms. For example, particular embodiments may trigger low-effort active assessment tasks if the user's pulmonary condition is severe. In general, a user suffering from pulmonary disease may become limited in their ability to perform activities as their condition worsens, limiting their ability to perform some tasks such as a 6MWT. Thus, particular embodiments may select active tasks for the user to perform based on the severity of the user's pulmonary condition.

In FIG. 3, step 306 may submit a request for the user to provide user data. As an example, the active assessment protocol may determine that the appropriate tasks are tidal breathing and an A-vowel task. In this example, a request for the user to submit tidal breathing data and A-vowel sound data may be made by the client device. In FIG. 3, step 308 may receive sensor data resulting from the request. In the previous example, sensor data resulting from the request for the user to provide tidal breathing and A-vowel sound data may be received. In FIG. 3, step 310 may determine a combination of features to be extracted. Different combinations of features used in measuring the user's pulmonary condition from active tasks affect the quality of the measurement. Some combinations of features may be more accurate than other combinations. In FIG. 3, step 312 may extract the combination of features. In FIG. 3, step 314 may determine pulmonary condition. Pulmonary condition may be determined based at least partly on features or symptoms extracted from passive monitoring. Relevant features or symptoms include one or more of frequency of the user's coughs as compared to a threshold, the presence of wheezing in the user's breathing, or the user's oxygen saturation as compared to a threshold.

In particular embodiments, tidal breathing task may be performed for one minute. Features extracted from tidal breathing data may include one or more of: mean, kurtosis, skewness, variance of inhalation, exhalation, inhale/exhale ratio, respiration rate, HR, HRV, or SpO2. Particular embodiments classify patient severity as mild, moderate, or severe using one or more suitable classifiers. For example, a Random Forest classifier with k-fold cross validation may be used to classify the severity of the user's pulmonary condition.

In particular embodiments, active assessment tasks may include a combination of tidal breathing, e.g., for one minute, and an A-vowel sound test. Features extracted from this combination may include one or more of: mean, kurtosis, skewness, variance of RR (the interval, in time, between two consecutive heartbeats), HR, HRV, SpO2, inhale/exhale ratio, inhale sound, envelop, or duration. In particular embodiments, active assessment tasks may include a combination of tidal breathing, e.g., for one minute, and a blowing exhale test. Features extracted from this combination may include one or more of: mean, kurtosis, skewness, variance of RR, HR, HRV, SpO2, inhale/exhale ratio, inhale sound pattern, or LPC. In particular embodiments, active assessment tasks may include a combination of tidal breathing, e.g., for one minute, and speech, e.g., for one minute. Features extracted from this combination may include one or more of: mean, kurtosis, skewness, variance of RR, HR, HRV, SpO2, inhale/exhale ratio, inhale sound pattern, or pause time between speech sounds.

In particular embodiments, active assessment tasks may include a combination of tidal breathing, e.g., for one minute, and a 6MWT. Features extracted from this combination may include one or more of: mean, kurtosis, skewness, variance of RR, HR, HRV, SpO2, inhale/exhale ratio, inhale sound pattern, or walk speed. particular embodiments, active assessment tasks may include a combination of tidal breathing, e.g., for one minute, an A-vowel sound test, and speech, e.g., for one minute. Features extracted from this combination may include one or more of: mean, kurtosis, skewness, variance of RR, HR, HRV, SpO2, inhale/exhale ratio, inhale sound pattern, envelop, duration, shimmer, jitter, or temporal trends. In particular embodiments, active assessment tasks may include a combination of speech, e.g., for one minute, and an A-vowel sound test. Features extracted from this combination include one or more of: mean, kurtosis, skewness, variance of shimmer, jitter, pause time, envelop, inhale/exhale ratio, or inhale sound pattern.

Particular embodiments may access time series data resulting from the user performance of active assessment tasks and detect the segment of time series data corresponding to the task performance. Embodiments may then determine the combination of tasks that were performed, determine the combination of features to be extracted from the combination of tasks, and compute the quality of the pulmonary condition measurement based on the determined combination of features.

Particular embodiments employ an A-vowel sound test, which may prompt the user to perform an A-vowel sound. Sound data of the A-vowel sound may be captured using a microphone on a mobile device. The sound signal may be normalized to account for variation in distance between the microphone and the sound's source. The A-vowel sound segment may then be isolated from other sounds, such as sounds in the background (e.g. a dog barking, the user coughing, or the user or other persons speaking). A feature vector may be computed from the A-vowel audio segment. Features may include both time domain and frequency domain features. Time domain and frequency domain features may be determined by a machine learning algorithm, in particular embodiments. Features may include one or more of: duration, envelop, area under the envelop, zero crossing rate, energy, entropy, spectrogram, mel-frequency cepstrum coefficients, or linear predictive coding. In particular embodiments, important features may be selected using Principal Component Analysis (PCA) based on feature transformation, correlation, or mutual information. The feature vector may be mapped using spirometer data to train and validate regression models for estimating parameters relevant to pulmonary condition (e.g., FEV1, FVC, FEV1/FVC ratio, and their changes). FEV1/FVC ratio is an indicator of the presence of lung obstruction, and FEV1 is an indicator of the severity of the lung obstruction.

A-vowel sound audio acoustic characteristics may be analyzed using raw signals and corresponding spectrograms. The acoustic data may be segmented into segmented windows, and the Short-Time Fourier Transformation (STFT) may be computed for one or more of the segmented windows. Particular embodiments may use a sliding Hann window of length 512 samples with a 50% overlap. Particular embodiments may segment the acoustic data into segmented windows of 200 ms frames. One or more of the following statistical functions may be computed for each frame: the audio signal's mean, variance, skewness, kurtosis, and power. In the context of particular embodiments, n represents the total length of the audio signal in milliseconds. In particular embodiments, the feature vectors may have a number of dimensions equal to the number of segmented window frames multiplied by the number of statistical functions computed for each frame ((n/frame length)×(number of statistical functions computed)). In particular embodiments, features include one or more of envelop, time domain features, spectral features, shimmer, jitter and temporal evolution features. In particular embodiments, the spectrogram may then be computed as the magnitude squared of the STFT. The example equations below illustrate techniques for computing the STFT and spectrogram, respectively.

$$X[n, k] = \sum_{m=0}^{W-1} x[m] \cdot w[n-m] \cdot e^{-i\frac{2\pi k}{N}m}$$

$$\text{Spectrogram}\{x(t)\}(n, k) = |X[n, k]|^2$$

Particular embodiments may determine whether the user would benefit from breathing exercises such as pursed lip breathing, based on the user's pulmonary condition. Embodiments may trigger breathing exercises for the user to perform, and suggested exercises may be presented to the user on a display of the user's client device. Embodiments may also communicate with the user's caregiver(s) information about the user's pulmonary assessment, such as any of the information discussed herein.

Particular embodiments may store and analyze data computed from passive assessment and active assessment over time. Particular embodiments may use features extracted from natural speech to detect the severity of pulmonary disease, capture adverse trends, or predict exacerbation events. For example, embodiments may track the user's FEV1% value over time. Data tracked over time may be used for detection of deterioration and may be valuable to prompt intervention. For example, a 20% drop in FEV1% is clinically considered deterioration. Embodiments may assess pulmonary condition using tracked data using a regression or classification model. Regression techniques may be used to match natural speech features to medical measures of severity (e.g., FEV1 ratio score as detected by a spirometer pulmonary function test). Particular embodiments may capture adverse trends and predict exacerbation events using one or more of: longitudinal monitoring of data, contextual information, and user inputs. Particular embodiments may build an adaptive learning model.

Particular embodiments may incorporate a severity estimation regression model for one or more classes of subject (e.g., healthy subject or pulmonary patient). These embodiments may further compute the probability that the user falls into a particular class of subject. For example, these embodiments may compute the probability that the user is in the "healthy" class. Particular embodiments may use the computed probabilities to calculate a probable regression model.

For example, the example equation below illustrates one technique for assembling regression model for more accurate FEV1% estimation.

Let $R_H$ and $R_P$ be regression model trained on healthy participants data and patients data respectively. Define C={healthy, patient} be the class of participants. Let M:F→C be a classifier that predicts, a person, whether healthy or patient from A-vowel segment. Suppose M also produces the probability of healthy $p_H$, and the probability of patient, $p_P$. By the law of probability, $p_H+p_P=1$. Then, $$R(f)=p_H*R_H(f)+p_P*R_P(f)$$

Figure 4:
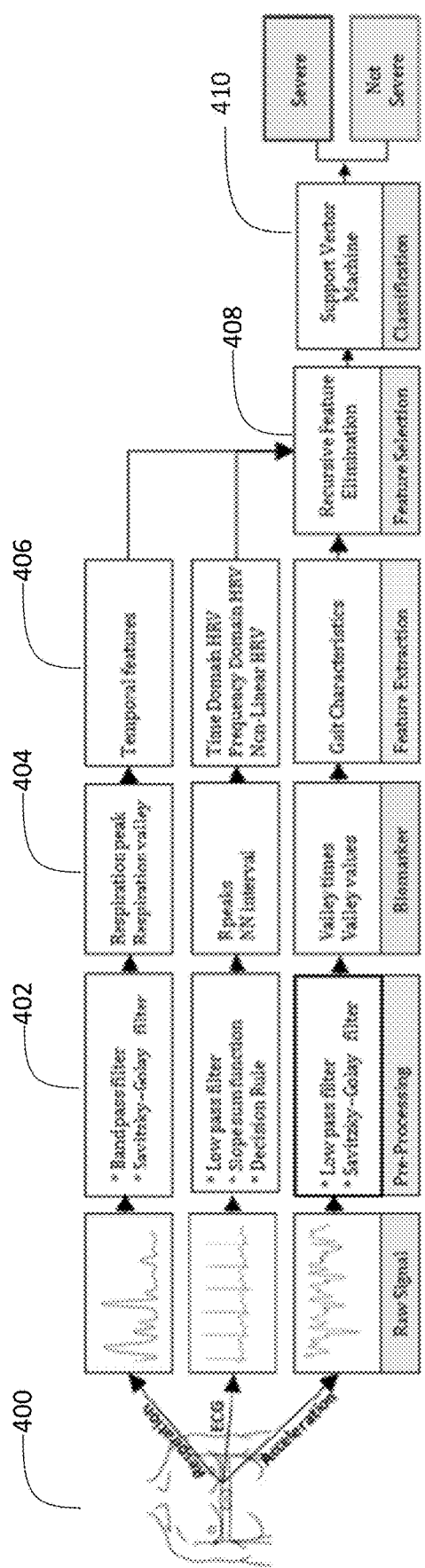
FIG. 4 illustrates an example method for signal processing and feature extraction.

Particular embodiments may use an analysis of sensor data in conjunction with machine learning algorithms to predict the severity of the user's pulmonary condition. FIG. 4 illustrates a method for signal processing and feature extraction. At step 400, sensor data may be collected by a chest band or other wearable device. The user may, for example, wear the wearable device while performing a 6MWT. As illustrated in FIG. 6, sensor data collected by the wearable device may include single channel respiration, ECG, and three channel acceleration data. Acceleration sensor data can be useful for monitoring the user's walking pattern and to extract gait and other related features.

In one example, the sampling frequency for the ECG signal may be 250 Hz, the respiration signal sampling frequency may be 25 Hz, and the sampling frequency for the acceleration sensor may be 100 Hz. At step 402, the raw signal is pre-processed using one or more types of filter. The filter could be a band pass filter, a Savitzky-Golay filter, a low pass filter, a slope sum fraction filter, or a decision rule filter. In one example, the acceleration data raw signal is pre-processed using a low pass filter. At step 404, acceleration data is further processed by detecting valleys to facilitate feature extraction. At step 406, features are extracted. In one example, the features extracted from acceleration data are gait characteristics, which have been extracted using vertical axis data. The features related to gait characteristics may include step time, step count, cadence, standard deviation in step time, and coefficient of variation in step time.

In one example, respiration data raw signal is pre-processed using a band pass filter. The upper and lower bounds of the band pass filter, in one example, may be 0.2 Hz and 0.8 Hz, respectively. Then, the data may be pre-processed through a Savitzky-Golay filter, which may be used for smoothing out the signal. At step 406 in one example, temporal features are extracted from the respiration data. Respiration features may be mean respiration rate, standard deviation in respiration rate, root mean square of successive standard deviation in respiration rate, or logarithmic root mean square of successive standard deviation. In one example, ECG data may be pre-processed at step 402 using a band pass filter. The upper and lower bounds of the band pass filter, in one embodiment, may be 0.5 Hz and 125 Hz, respectively. Then, at step 404 a Pan-Tompkins algorithm may be used for the R peak detection. The RR series may be pre-processed by removing outliers and ectopic beats to obtain normal RR intervals or NN (normal-to-normal) intervals. Interpolation may be used to fill missing or discarded beat positions. A 3rd order moving average filter may be used to remove noise. The features related to ECG are the linear features of time domain, frequency domain, and non-linear HRV, and the non-linear features of transverse standard deviation, longitudinal standard deviation, ratio of transverse and longitudinal standard deviations, and the ellipse area from a Poincare plot.

At step 408 of FIG. 4, features may be selected for use in classification. Feature selection may be performed by an algorithm, such as Recursive Feature Elimination (RFE) with Scikit-learn. Reducing the dimension of features for use in classification algorithms improves efficiency and computational complexity, especially when data may come from wearable devices. Filter-based methods, such as RFE, may be computationally less expensive than wrapper-based methods and can help avoid overfitting. In particular embodiments, feature selection algorithms may rank the top 15 features. Top features may be selected and used in the classification methods.

At step 410 of FIG. 4, the user may be classified into a particular class of subject (e.g. severe patient or non-severe patient). This classification may be computed using sensor data collected during the user's 6MWT, which may include data collected using a wearable device such as a chest band. Classification models which may be implemented include Logistic regression, Support Vector Machines (SVM), Random forest, and AdaBoost. Algorithms may be trained using a training set and a test set. 5-fold cross-validation may be used on the training set data. Grid search method from the Scikit-learn model may be used with 10-fold cross-validation to tune hyper-parameters and to choose a kernel for an SVM classification model. For the AdaBoost classification model, maximum depth may be limited to avoid overfitting. In one example, the maximum depth limit may be 3 with 50 estimators. "SAMME" may be used as a boosting algorithm. Particular embodiments may use a random forest classifier to classify the user as a healthy subject or a pulmonary patient. The random forest classifier may use as inputs one or more of: pause time, pause frequency, absolute shimmer, relative shimmer, absolute jitter, or relative jitter.

Particular embodiments may detect and extract features from activities such as swimming, running, or sleep. Other embodiments may consider sports activities (e.g., soccer, tennis, badminton) to extract differential features. Other embodiments may consider whether the user is engaged in forced speech, where the user is speaking in a noisy environment (e.g., a restaurant, or in an environment where a TV or radio is on) or is speaking to more than one person. Those contexts, which require the user to speak with increased force to be intelligible, can be used to detect features related to the user's pulmonary condition.

Particular embodiments may incorporate wearable devices for collection of sensor data. Wearable devices may include one or more of: a chest band, smart patch, smart clothing, smart waist belt, or a device attached around the chest or around the waist. Particular embodiments may collect electrocardiogram (ECG) data or respiratory inductive plethysmograph (RIP) data in place of or as a supplement to PPG data. Particular embodiments may incorporate contactless sensing devices embedded in smart spaces such as an autonomous vehicle, smart-home, or smart elderly care facility. Contactless devices may extract the primal and differential features from millimeter-wave or radio frequency (RF) signal data.

Particular embodiments may take into account the user's regular routine. For example, particular embodiments may compute a baseline routine using topic modeling, knowledge graphs, rule mining, machine learning, or any suitable combination therefore. Example baseline routines may include sleep duration, step count, speech duration, commute duration, or the number of places visited in a week. Particular embodiments may detect deviations from the baseline routine and may trigger an active assessment for the user to perform to confirm whether the deviation is due to lung condition or due to other factors. Active assessment may be triggered based on the level of deviation from the baseline routine, such as whether the deviation is significant or mild. In particular embodiments, if the deviation is determined to be due to lung deterioration, the user may be alerted (e.g., via a GUI on a display of the user's client device) that the user should take medication, or the embodiment may alert the user's primary care physician to allow for intervention and prevention of further deterioration.

Figure 5:
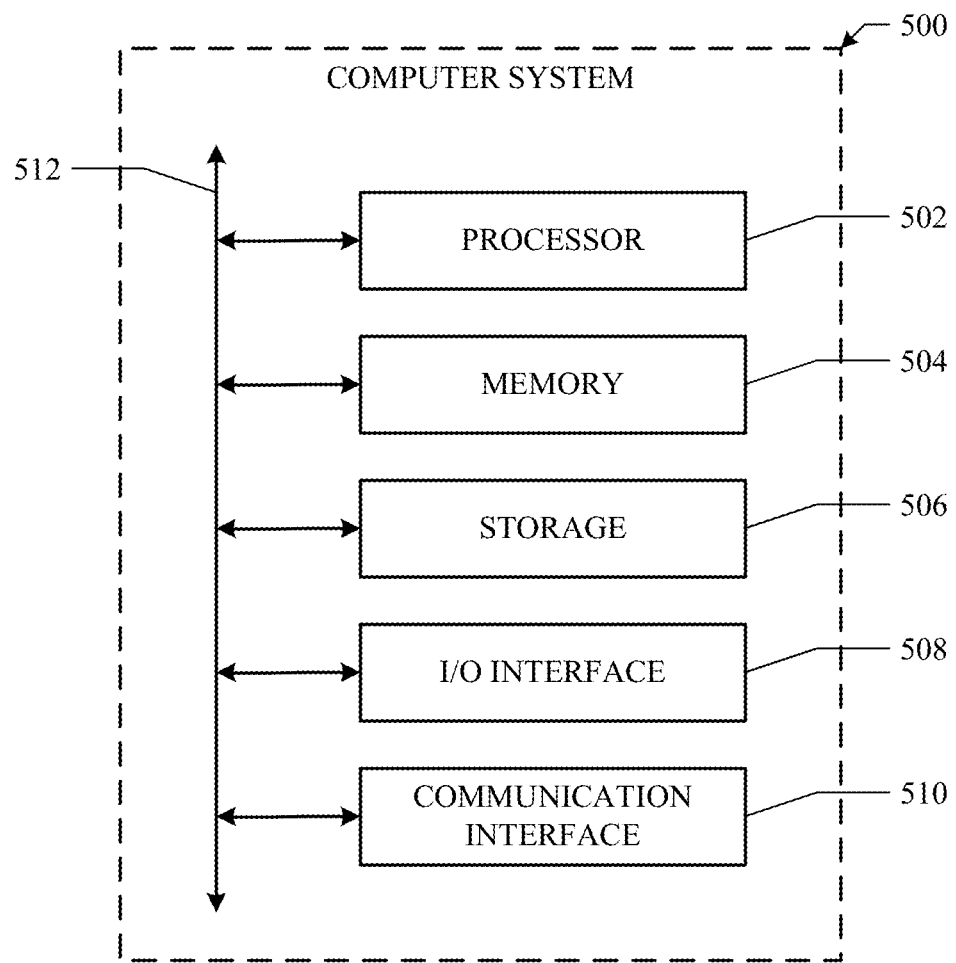
FIG. 5 illustrates an example computer system.

FIG. 5 illustrates an example computer system 500. In particular embodiments, one or more computer systems 500 perform one or more steps of one or more methods described or illustrated herein. In particular embodiments, one or more computer systems 500 provide functionality described or illustrated herein. In particular embodiments, software running on one or more computer systems 500 performs one or more steps of one or more methods described or illustrated herein or provides functionality described or illustrated herein. Particular embodiments include one or more portions of one or more computer systems 500. Herein, reference to a computer system may encompass a computing device, and vice versa, where appropriate. Moreover, reference to a computer system may encompass one or more computer systems, where appropriate.

This disclosure contemplates any suitable number of computer systems 500. This disclosure contemplates computer system 500 taking any suitable physical form. As example and not by way of limitation, computer system 500 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, an augmented/virtual reality device, or a combination of two or more of these. Where appropriate, computer system 500 may include one or more computer systems 500; be unitary or distributed; span multiple locations; span multiple machines; span multiple data centers; or reside in a cloud, which may include one or more cloud components in one or more networks. Where appropriate, one or more computer systems 500 may perform without substantial spatial or temporal limitation one or more steps of one or more methods described or illustrated herein. As an example and not by way of limitation, one or more computer systems 500 may perform in real time or in batch mode one or more steps of one or more methods described or illustrated herein. One or more computer systems 500 may perform at different times or at different locations one or more steps of one or more methods described or illustrated herein, where appropriate.

In particular embodiments, computer system 500 includes a processor 502, memory 504, storage 506, an input/output (I/O) interface 508, a communication interface 510, and a bus 512. Although this disclosure describes and illustrates a particular computer system having a particular number of particular components in a particular arrangement, this disclosure contemplates any suitable computer system having any suitable number of any suitable components in any suitable arrangement.

In particular embodiments, processor 502 includes hardware for executing instructions, such as those making up a computer program. As an example and not by way of limitation, to execute instructions, processor 502 may retrieve (or fetch) the instructions from an internal register, an internal cache, memory 504, or storage 506; decode and execute them; and then write one or more results to an internal register, an internal cache, memory 504, or storage 506. In particular embodiments, processor 502 may include one or more internal caches for data, instructions, or addresses. This disclosure contemplates processor 502 including any suitable number of any suitable internal caches, where appropriate. As an example and not by way of limitation, processor 502 may include one or more instruction caches, one or more data caches, and one or more translation lookaside buffers (TLBs). Instructions in the instruction caches may be copies of instructions in memory 504 or storage 506, and the instruction caches may speed up retrieval of those instructions by processor 502. Data in the data caches may be copies of data in memory 504 or storage 506 for instructions executing at processor 502 to operate on; the results of previous instructions executed at processor 502 for access by subsequent instructions executing at processor 502 or for writing to memory 504 or storage 506; or other suitable data. The data caches may speed up read or write operations by processor 502. The TLBs may speed up virtual-address translation for processor 502. In particular embodiments, processor 502 may include one or more internal registers for data, instructions, or addresses. This disclosure contemplates processor 502 including any suitable number of any suitable internal registers, where appropriate. Where appropriate, processor 502 may include one or more arithmetic logic units (ALUs); be a multi-core processor; or include one or more processors 502. Although this disclosure describes and illustrates a particular processor, this disclosure contemplates any suitable processor.

In particular embodiments, memory 504 includes main memory for storing instructions for processor 502 to execute or data for processor 502 to operate on. As an example and not by way of limitation, computer system 500 may load instructions from storage 506 or another source (such as, for example, another computer system 500) to memory 504. Processor 502 may then load the instructions from memory 504 to an internal register or internal cache. To execute the instructions, processor 502 may retrieve the instructions from the internal register or internal cache and decode them. During or after execution of the instructions, processor 502 may write one or more results (which may be intermediate or final results) to the internal register or internal cache. Processor 502 may then write one or more of those results to memory 504. In particular embodiments, processor 502 executes only instructions in one or more internal registers or internal caches or in memory 504 (as opposed to storage 506 or elsewhere) and operates only on data in one or more internal registers or internal caches or in memory 504 (as opposed to storage 506 or elsewhere). One or more memory buses (which may each include an address bus and a data bus) may couple processor 502 to memory 505. Bus 512 may include one or more memory buses, as described below. In particular embodiments, one or more memory management units (MMUs) reside between processor 502 and memory 504 and facilitate accesses to memory 504 requested by processor 502. In particular embodiments, memory 504 includes random access memory (RAM). This RAM may be volatile memory, where appropriate. Where appropriate, this RAM may be dynamic RAM (DRAM) or static RAM (SRAM). Moreover, where appropriate, this RAM may be single-ported or multi-ported RAM. This disclosure contemplates any suitable RAM. Memory 504 may include one or more memories 504, where appropriate. Although this disclosure describes and illustrates particular memory, this disclosure contemplates any suitable memory.

In particular embodiments, storage 506 includes mass storage for data or instructions. As an example and not by way of limitation, storage 506 may include a hard disk drive (HDD), a floppy disk drive, flash memory, an optical disc, a magneto-optical disc, magnetic tape, or a Universal Serial Bus (USB) drive or a combination of two or more of these. Storage 506 may include removable or non-removable (or fixed) media, where appropriate. Storage 506 may be internal or external to computer system 500, where appropriate. In particular embodiments, storage 506 is non-volatile, solid-state memory. In particular embodiments, storage 506 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 506 taking any suitable physical form. Storage 506 may include one or more storage control units facilitating communication between processor 502 and storage 506, where appropriate. Where appropriate, storage 506 may include one or more storages 506. Although this disclosure describes and illustrates particular storage, this disclosure contemplates any suitable storage.

In particular embodiments, I/O interface 508 includes hardware, software, or both, providing one or more interfaces for communication between computer system 500 and one or more I/O devices. Computer system 500 may include one or more of these I/O devices, where appropriate. One or more of these I/O devices may enable communication between a person and computer system 500. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 508 for them. Where appropriate, I/O interface 508 may include one or more device or software drivers enabling processor 502 to drive one or more of these I/O devices. I/O interface 508 may include one or more I/O interfaces 508, where appropriate. Although this disclosure describes and illustrates a particular I/O interface, this disclosure contemplates any suitable I/O interface.

In particular embodiments, communication interface 510 includes hardware, software, or both providing one or more interfaces for communication (such as, for example, packet-based communication) between computer system 500 and one or more other computer systems 500 or one or more networks. As an example and not by way of limitation, communication interface 510 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 510 for it. As an example and not by way of limitation, computer system 500 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 500 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 500 may include any suitable communication interface 510 for any of these networks, where appropriate. Communication interface 510 may include one or more communication interfaces 510, where appropriate. Although this disclosure describes and illustrates a particular communication interface, this disclosure contemplates any suitable communication interface.

In particular embodiments, bus 512 includes hardware, software, or both coupling components of computer system 500 to each other. As an example and not by way of limitation, bus 512 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 512 may include one or more buses 512, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

Herein, "automatically" and its derivatives means "without human intervention," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

What is claimed is:

1. A method comprising:
   detecting, by a sensor of a client device corresponding to a user, sensor data based on one or more of acoustic signals, movement, or heart activity of the user;
   by a computing device:
   accessing the sensor data from the sensor of the client device corresponding to the user;
   determining one or more segments of the sensor data;
   selecting at least one segment of the one or more segments of the sensor data;
   determining, based at least on the at least one selected segment of sensor data, one or more features corresponding to the user's pulmonary condition;
   determining, based at least on the determined one or more features, a passive assessment of the user's pulmonary condition, wherein the passive assessment of the user's pulmonary condition comprises a determination of the user's pulmonary obstruction;
   determining whether a number of passive assessments of the user's pulmonary obstruction, each passive assessment comprising a separate determination of the user's pulmonary obstruction, in a particular time period is less than a threshold number of passive assessments of the user's pulmonary obstruction; and
   in response to a determination that the number of passive assessments of the user's pulmonary obstruction in the particular time period is less than the threshold number of passive assessments, submitting, to the client device, a request for the user to provide user data for an active assessment of the user's pulmonary condition.

2. The method of claim 1, further comprising:
   receiving, from the client device, the user data resulting from the request; and
   determining, from the user data resulting from the request, the active assessment of the user's pulmonary condition.

3. The method of claim 2, wherein the user data for the active assessment of the user's pulmonary condition comprises data from one or more actions of the user:
   blowing into the sensor of the client device or into a different sensor of the client device;
   providing an A-vowel sound;
   performing tidal breathing;
   speaking; or
   performing a 6MWT test.

4. The method of claim 1, further comprising:
   in response to the determination that the number of passive assessments in the particular time period is not less than the threshold number of passive assessments, determining, based on the passive assessment of the user's pulmonary condition and one or more previous assessments of the user's pulmonary condition, a trend of the user's pulmonary condition.

5. The method of claim 1, wherein the one or more segments of the sensor data correspond to the user's pulmonary condition.

6. The method of claim 1, wherein selecting the at least one segment of the sensor data corresponding to the user's pulmonary condition comprises:
   detecting, based on the sensor data, an activity of the user;
   segmenting, based on the sensor data, the activity of the user into a plurality of activity segments;
   determining, for each activity segment and based on one or more criteria, whether the activity segment contains sufficient data for performing the passive assessment; and
   selecting each segment of the sensor data that corresponds to each activity segment that contains the sufficient data for performing the passive assessment.

7. The method of claim 1, wherein the one or more features corresponding to the user's pulmonary condition comprise primal features.

8. The method of claim 7, wherein the primal features are determined for each of a plurality of the selected segments.

9. The method of claim 1, wherein:
   the one or more features corresponding to the user's pulmonary condition comprise differential features; and
   the differential features are determined by comparing primal features from a plurality of different time periods.

10. The method of claim 9, wherein the plurality of different time periods comprise:
    a first time period corresponding to a start of an activity corresponding to the determined one or more segments; and
    a second time period corresponding to an end of the activity.

11. The method of claim 9, wherein the plurality of different time periods comprise:
    a first time period corresponding to a previous pulmonary assessment of the user's pulmonary condition; and
    a second time period corresponding to a current pulmonary assessment of the user's pulmonary condition.

12. The method of claim 1, wherein determining the passive assessment of the user's pulmonary condition comprises estimating a severity of the pulmonary obstruction.

13. The method of claim 1, wherein the sensor comprises one or more of a motion sensor, a heart sensor, or an acoustic sensor.

14. One or more non-transitory computer-readable storage media embodying instructions that are operable, when executed by a processor to:
   cause a sensor of a client device corresponding to a user to detect sensor data based on one or more of acoustic signals, movement, or heart activity of the user;
   access the sensor data from the sensor of the client device corresponding to the user;
   determine one or more segments of the sensor data;
   select at least one segment of the sensor data;
   determine, based at least on the at least one selected segment of the sensor data, one or more features corresponding to the user's pulmonary condition;
   determine, based at least on the determined features, a passive assessment of the user's pulmonary condition, wherein the passive assessment of the user's pulmonary condition comprises a determination of the user's pulmonary obstruction;

determine whether a number of passive assessments of the user's pulmonary obstruction, each passive assessment comprising a separate determination of the user's pulmonary obstruction, in a particular time period is less than a threshold number of passive assessments of the user's pulmonary obstruction; and in response to a determination that the number of passive assessments of the user's pulmonary obstruction in the particular time period is less than the threshold number of passive assessments, submit, to the client device, a request for the user to provide user data for an active assessment of the user's pulmonary condition.

15. The media of claim 14, wherein the instructions are further operable, when executed by the processor, to:

detect, based on the sensor data, an activity of the user;

segment, based on the sensor data, the activity of the user into a plurality of activity segments;

determine, for each activity segment and based on one or more criteria, whether the activity segment contains sufficient data for performing the passive assessment; and select each segment of the sensor data that corresponds to each activity segment that contains the sufficient data for performing the passive assessment.

16. An apparatus comprising:

a sensor of a client device corresponding to a user, the sensor configured to detect sensor data based on one or more of acoustic signals, movement, or heart activity of the user;

one or more non-transitory computer-readable storage media embodying instructions; and one or more processors coupled to the storage media and to the sensor, the processors being operable to execute the instructions to:

access the sensor data from the sensor of the client device corresponding to the user;

determine one or more segments of the sensor data;

select at least one segment of the sensor data;

determine, based at least on the at least one selected segment of the sensor data, one or more features corresponding to the user's pulmonary condition;

determine, based at least on the determined features, a passive assessment of the user's pulmonary condition, wherein the passive assessment of the user's pulmonary condition comprises a determination of the user's pulmonary obstruction;

determine whether a number of passive assessments of the user's pulmonary obstruction, each passive assessment comprising a separate determination of the user's pulmonary obstruction, in a particular time period is less than a threshold number of passive assessments of the user's pulmonary obstruction; and in response to a determination that the number of passive assessments of the user's pulmonary obstruction in the particular time period is less than the threshold number of passive assessments, submit, to the client device, a request for the user to provide user data for an active assessment of the user's pulmonary condition.

17. The apparatus of claim 16, wherein the processors are further operable to execute the instructions to:

detect, based on the sensor data, an activity of the user;

segment, based on the sensor data, the activity of the user;

determine, for each segment and based on one or more criteria, whether the segment contains sufficient data for performing the passive assessment; and select each segment of the sensor data that corresponds to each segment that contains the sufficient data for performing the passive assessment.

18. The apparatus of claim 16, wherein:

the one or more features corresponding to the user's pulmonary condition comprise differential features; and the differential features are determined by comparing primal features from a plurality of different time periods.

19. The apparatus of claim 18, wherein the plurality of different time periods comprise:

a first time period corresponding to a start of an activity corresponding to the determined one or more segments; and a second time period corresponding to an end of the activity.

* * * * *